US005643556A

United States Patent [19]
Gilchrest et al.

[11] Patent Number: 5,643,556
[45] Date of Patent: *Jul. 1, 1997

[54] STIMULATION OF TANNING BY DNA FRAGMENTS OR SINGLE-STRANDED DNA

[75] Inventors: Barbara A. Gilchrest, Brookline; Mina Yaar, Sharon; Mark Eller, Boston, all of Mass.

[73] Assignee: Trustees of Boston University, Boston, Mass.

[*] Notice: The term of this patent shall not extend beyond the expiration date of Pat. No. 5,470,577.

[21] Appl. No.: 493,251

[22] Filed: Jun. 6, 1995

Related U.S. Application Data

[63] Continuation of PCT/US94/07647, Jul. 7, 1994, which is a continuation of Ser. No. 88,251, Jul. 7, 1993, Pat. No. 5,470,577.

[51] Int. Cl.$^6$ .......................... A61K 48/00; A61K 7/42; A61K 47/30
[52] U.S. Cl. .......................... 424/59; 424/520; 424/450; 514/44
[58] Field of Search .......................... 435/91.1, 172.3, 435/6; 514/44, 946, 947; 935/62, 54, 33, 34; 536/23.1, 24.5; 424/59, 450, 520

[56] References Cited

U.S. PATENT DOCUMENTS

| | | | |
|---|---|---|---|
| 3,937,809 | 2/1976 | Jacobi | 424/60 |
| 4,419,343 | 12/1983 | Pauly | 424/59 |
| 4,866,038 | 9/1989 | Hruby et al. | 514/14 |
| 4,956,489 | 9/1990 | Auriol et al. | 560/40 |
| 5,352,458 | 10/1994 | Yarosh | 424/450 |

FOREIGN PATENT DOCUMENTS

| | | |
|---|---|---|
| 0 313 446 | 10/1988 | European Pat. Off. . |
| 0 318 369 | 11/1988 | European Pat. Off. . |
| 0 386 680 | 5/1990 | European Pat. Off. . |
| 0416677A1 | 3/1991 | European Pat. Off. . |
| 0484199A1 | 5/1992 | European Pat. Off. . |
| 2511243 | 2/1983 | France . |
| 63-183518 | 7/1988 | Japan . |
| 63-301810 | 12/1988 | Japan . |
| WO91/07168 | 5/1991 | WIPO . |

OTHER PUBLICATIONS

Friedmann, P.S., et al., "Ultraviolet radiation directly induces pigment production by cultured human melanocytes", *J. Cell. Physiol.* 133(1):88–94 (1987).

Bonte, F., et al., "Kaempferol Liposome Activity on Skin Melanogenesis", *Congr. Int. Technol. Pharm.* 5th(3):404–407 (1989).

Niggli, H.J., et al., "Determination of Cytosine–Cytosine Photodimers in DNA of Cloudman S91 Melanoma Cells Using High Pressure Liquid Chromatography", *Photochem. & Photobiol.* 55(5):793–796 (1992).

Niggli, H.J., et al., "Sunlight–Induced Pyrimidine Dimers in Human Skin Fibroblasts in Comparison with Dimerization After Artificial UV–Irradiation", *Photochem. & Photobiol.* 48(3):353–356. (1988).

Niggli, H.J., et al., "Cyclobutane–Type Pyrimidine Photodimer Formation and Excision in Human Skin Fibroblasts After Irradiation With 313–nm Ultraviolet Light", *Biochem.* 22:1390–1395 (1983).

Niggli, H.J., "Comparative Studies on the Correlation Between Pyrimidine Dimer Formation and Tyrosinase Activity in Cloudman S91 Melanoma Cells After Ultraviolet–Irradiation", *Photochem. & Photobiol.* 52 (3) :519–524 (1990).

Niggli, H.J., et al., "Nucleosomal Distribution of Thymine Photodimers Following Far– and Near–Ultraviolet Irradiation", *Biochem. and Biophys. Research Communications* 105(3):1215–1223 (1982).

Sugitani, Yoshinori et al., "Red Shift in Photoacoustic Ultraviolet Absorption Spectra of Solid Purine Bases, Nucleosides and Nucleotides," *Analytical Sciences* 4:215–217 (1988).

Yaar, Mina and Gilchrest, Barbara A., "Human Melanocyte Growth and Differentiation: A Decade of New Data," *Journal for Investigative Dermatology, Inc.* 97(4):611–617 (1991).

Yarosh, Daniel B. et al., "Enhancement of DNA repair of UV damage in mouse and human skin by liposomes containing a DNA repair enzyme," *J. Soc. Cosmet. Chem.*, 41:85–92 (1990).

Sigma Chemical Company, Biochemicals Organic Compounds for Research and Diagnostic Reagents, 1992. Dec. 1991.

*Primary Examiner*—Jasemine C. Chambers
*Assistant Examiner*—Karen M. Hauda
*Attorney, Agent, or Firm*—Hamilton, Brook, Smith & Reynolds, P.C.

[57] ABSTRACT

A method of stimulating pigment production in mammalian skin, as well as protecting mammalian skin against ultraviolet damage, is disclosed. Also disclosed is a method of stimulating pigment production in mammalian cells, a method of stimulating melanogenesis in mammalian melanocytes, and a culture medium for stimulating melanin production. Preparations useful in the present methods are additionally disclosed. The methods comprise administering to the epidermis or to the cells DNA fragments, either single- or double-stranded, or a mixture of both, or deoxynucleotides, dinucleotides, or dinucleotide dimers, in an appropriate vehicle, such as a liposomal preparation or propylene glycol. The preparations include DNA fragments, deoxynucleotides, dinucleotides, or dinucleotide dimers and an appropriate delivery vehicle, such as liposomes or a propylene glycol. The DNA fragments, deoxynucleotides, or dinucleotides used in the methods or in the preparations can be ultraviolet-irradiated. The preparations are sunlight-independent tanning or melanogenesis-stimulating agent.

22 Claims, 8 Drawing Sheets

STIMULATION OF TANNING BY DNA FRAGMENTS OR SINGLE-STRANDED DNA

RELATED APPLICATIONS

This is a continuation of International Application PCT/US94/07647, which designated the United States, with an international filing date of Jul. 7, 1994, and is being filed under the provisions of 35 U.S.C. §111, and which claims priority to U.S. Ser. No. 08/088,251, filed Jul. 7, 1993, now U.S. Pat. No. 5,470,577, the entire teachings of which are incorporated herein by reference.

BACKGROUND OF THE INVENTION

Human skin consists of two layers, the uppermost of which is the epidermis. The epidermis encompasses many different cell types, including melanocytes and keratinocytes. Melanocytes are specialized cells in the basal layer of the epidermis which synthesize melanin; the melanin is then packaged into melanosomes and then transported into keratinocytes.

It has been known for centuries that exposure of skin to the sun results in tanning, the skin's major form of endogenous protection against subsequent skin damage from ultraviolet (UV) irradiation. Melanin, a polymer which serves as a filter with absorbance within the UV range, provides photoprotection for the individual. The peak action spectrum for this phenomenon is in the UV-B range, 290–305 nm; various morphologic and enzymatic changes occur at the cellular level in epidermal melanocytes in response to UV irradiation. Proteins and nucleic acids of the epidermis absorb UV-B rays, causing the production of thymine dimers, which are known to be formed by UV irradiation of nuclear DNA and to be excised from the DNA strand by the action of highly specific enzymes, including endonucleases. If not removed, these dimers can stall DNA replication forks generating regions of single-stranded DNA. Failure to remove thymine dimers and other DNA mutations in the genome may lead to somatic mutations resulting in carcinogenesis.

In bacteria it is known that the DNA fragments released from stalled replication forks can interact with nuclear proteins which then regulate the expression of specific genes in the DNA as part of the organism's SOS response to UV damage. Bacteria do not tan, but tanning might reasonably be considered part of the analogous SOS response in mammalian skin. The precise stimulus for UV-induced tanning, however, remains unknown.

SUMMARY OF THE INVENTION

The current invention pertains to a method of increasing the pigmentation in skin. It consists of applying topically to the epidermis DNA fragments, either single- or double-stranded, or a mixture of both single- and double-stranded DNA fragments, or deoxynucleotides, dinucleotides, or dinucleotide dimers, notably in a delivery vehicle such as in a liposome preparation, such that the DNA fragments, deoxynucleotides, dinucleotides, or dinucleotide dimers are available to the melanocytes. The DNA fragments, either single- or double-stranded, or the mixture of both single-and double-stranded DNA fragments, or deoxynucleotides, or dinucleotides can be ultraviolet-irradiated. The method results in the stimulation of a tanning response equivalent to that produced by sun exposure, but without necessity of actual sun exposure, and thereby avoids subjecting the skin to the carcinogenic action of UV irradiation. The invention additionally pertains to a method of stimulating pigment production in melanocytes by applying to the cells DNA fragments, either single- or double-stranded, or a mixture of both single- and double-stranded DNA fragments, or deoxynucleotides, dinucleotides, or dinucleotide dimers. The invention further includes a culture medium for stimulating pigment production in melanocytes, comprising increasing melanin, the culture medium comprising an effective amount of DNA fragments, either single- or double-stranded, or a mixture of both single- and double-stranded DNA fragments, or deoxynucleotides, dinucleotides, or dinucleotide dimers. The invention also includes compositions useful in stimulating pigment production in skin, comprising DNA fragments, deoxynucleotides, dinucleotides or dinucleotide dimers notably in an appropriate delivery vehicle, such as liposomes.

Application of DNA fragments, deoxynucleotides, dinucleotides, or dinucleotide dimers by the method of the present invention results in a cosmetically pleasing tan that may also be protective against subsequent UV damage to the skin, including sunburn, photoaging, and development of skin cancer. The results are obtained even in the absence of exposure to sunlight. The current invention can also be used for stimulating pigment production for other purposes, such as to increase pigmentation in hypopigmented areas of the skin.

DETAILED DESCRIPTION OF THE INVENTION

The invention pertains to use of a preparation comprising DNA fragments, deoxynucleotides, dinucleotides, or dinucleotide dimers, as defined in the following description, for increasing pigmentation in mammalian skin by stimulating melanogenesis in melanocytes to form melanin pigments which are transferred to the keratinocytes. The invention also provides compositions comprising said DNA fragments, deoxynucleotides, dinucleotides, or dinucleotide dimers, for increasing skin pigmentation, as herein defined. The invention further comprises a method for stimulating skin pigment production comprising applying said DNA fragments, deoxynucleotides, dinucleotides, or dinucleotide dimers, as herein defined. No exposure to sunlight is necessary for the increase in pigmentation resulting from the uses, methods, and compositions of the current invention. The invention is thus useful for sunlight-independent skin tanning, as well as for pigmenting skin grafts, allografts, and autografts, both in vivo and in vitro, and also for treating hypopigmentation disorders such as vitiligo, albinism, piebaldism, and post-inflammatory hypopigmentation. Other advantageous invention embodiments are set forth in the claims, the content thereof being incorporated in its entirety in the present description by reference.

In one embodiment, DNA fragments, of approximately 2–200 bases in length, deoxynucleotides (single bases), dinucleotides, or dinucleotide dimers, are administered topically to the epidermis, in an appropriate vehicle, such as a liposome preparation or propylene glycol, in a quantity sufficient to stimulate melanin production. As used herein, "DNA fragments" refers to single-stranded DNA fragments, double-stranded DNA fragments, a mixture of both single- and double-stranded DNA fragments, or deoxynucleotides, dinucleotides, or dinucleotide dimers. "Deoxynucleotides" refers to either a single type of deoxynucleotide or a mixture of different deoxynucleotides. "Dinucleotides" can comprise a single type of nucleotide or different types of nucleotides, and can comprise different types of dinucleotides; in a preferred embodiment, the nucleotides of the dinucleotides are deoxynucleotides. Representative dinucleotides include d(pT)$_2$, d(pC)$_2$, d(pA)$_2$, d(pCpT), d(pTpC), d(CpT), d(TpC) and d(TpT), where T is thymine, C is cytosine, A is adenosine, d is deoxy, and p is phosphate (see Niggli, Photochem. Photobiol. 38(3): 353–356 (1988)). A combination of at least two or more of DNA fragments, deoxynucleotides, dinucleotides, and/or dinucleotide dimers can also be used. The DNA fragments, deoxynucleotides, or dinucleotides can be ultraviolet-irradiated. Such ultraviolet irradiation usually results in photodimerization between two adjacent pyrimidine residues (i.e., thymine (T) and cytosine (C)) present in the DNA fragments, or dinucleotides. One skilled in the art may refer to Biochemistry, (J. D. Rawn, Nail Patterson, Publisher, Carolina Biological Supply Company, North Carolina, 1989, pages 730–736). The DNA fragments, deoxynucleotides, dinucleotides, and dinucleotide dimers utilized in the current invention act as sunlight-independent active agents: the stimulation of pigmentation results even in the absence of exposure to sunlight.

The DNA fragments, deoxynucleotides, dinucleotides, or dinucleotide dimers can be obtained from any appropriate source, or can be synthetic DNA fragments, deoxynucleotides, dinucleotides, or dinucleotide dimers. For example, salmon sperm DNA can be dissolved in water, and then the mixture can be autoclaved to fragment the DNA. The delivery vehicle can be any appropriate vehicle which promotes the delivery of the DNA fragments, deoxynucleotides, dinucleotides, or dinucleotide dimers to the melanocytes. In one embodiment, a liposome preparation is used. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used.

Alternatively, the DNA fragments, deoxynucleotides, dinucleotides or dinucleotide dimers can be applied directly to the epidermis. In addition, the DNA fragments, deoxynucleotides, dinucleotides, or dinucleotide dimers can be applied in a vehicle which specifically targets melanocytes. For example, a membrane marker specific for melanocytes, such as melanocyte stimulating hormone (MSH), can be incorporated into a liposome containing the DNA fragments, deoxynucleotides, dinucleotides or dinucleotide dimers. Furthermore, according to an advantageous invention embodiment, the DNA fragments, deoxynucleotides, dinucleotides or dinucleotide dimers are used in combination with a diacyl glycerol. Preferred diacyl glycerols are 1,2-dioctanoyl glycerol, 1,2-didecanoyl glycerol, and 1-oleoyl-2-acetyl-glycerol. A preferred concentration of diacyl glycerol will usually range from 0.10 to 20.0 mM. In another advantageous embodiment, the DNA fragments, deoxynucleotides, dinucleotides or dinucleotide dimers are used in combination with an agent that stimulates the cyclic AMP pathway, such as isobutylmethylxanthine (IBMX). A preferred concentration of IBMX will usually range from 0.10 to 20.0 mM. Alternatively, the IBMX can be applied subsequently to the application of the DNA fragments, deoxynucleotides, dinucleotides or dinucleotide dimers.

The delivery vehicle can also contain perfumes, colorants, stabilizers, sunscreens, or other ingredients.

The preparation is applied topically to the skin surface at regular intervals, such as once or twice daily, in a suitable vehicle at an effective concentration, which will generally be approximately 0.1 µM to 1 mM or 0.05–10 mg/ml. Representative preferred concentrations include 100–300 µM, or 25–500 µM. The concentration will depend on the molecular weight of the fragments employed.

A similar such method is used to stimulate pigment production in mammalian cells, and particularly in melanocytes. In one embodiment, DNA fragments, either single- or double-stranded, or a mixture of both single- and double-stranded DNA fragments, or deoxynucleotides, dinucleotides, or dinucleotide dimers are applied to melanocytes in an appropriate vehicle, such as a liposome preparation or propylene glycol. It is believed that the increase in pigmentation results from stimulating melanogenesis by penetration of the invention DNA fragments inside the melanocytes and even inside the nuclei of the cells.

The current invention further encompasses a culture medium for stimulating melanin production in mammalian melanocytes, the medium comprising an effective amount of DNA fragments, either single-stranded, double-stranded, or a mixture of single- and double-stranded DNA fragments, deoxynucleotides, dinucleotides, or dinucleotide dimers. The DNA fragments, deoxynucleotides, or dinucleotides can also be ultraviolet-irradiated. The effective amount will generally be between 0.1–1 µM.

The invention is further illustrated by the following Examples.

EXAMPLE 1

Effect of DNA Fragments on the Pigmentation of S91 Cells

DNA for all experiments was fragmented salmon sperm DNA (Sigma Chemical Co.). Liposome preparations were obtained from the company Parfums Christian Dior.

In one experiment, S91 cells (a murine melanoma cell line) were plated at $2 \times 10^5$ cells per dish on 60 mm diameter culture dishes, in DME plus 10% calf serum (CS) at 37° C., and cultured for 24 hours (Day 1). On Day 2, the medium was changed, and cells were exposed to one of three additions: 100 µM empty liposomes ($A_1$); 100 µM liposomes containing UV-DNA (irradiated) ($B_1$); and 100 µM liposomes containing DNA (not irradiated) ($C_1$). The cells were then cultured for three days; on Day 5, the medium was changed and the cells were cultured for another three days in the presence of the respective additions. On Day 8 the cells were collected, and assayed for melanin.

Figure 1:
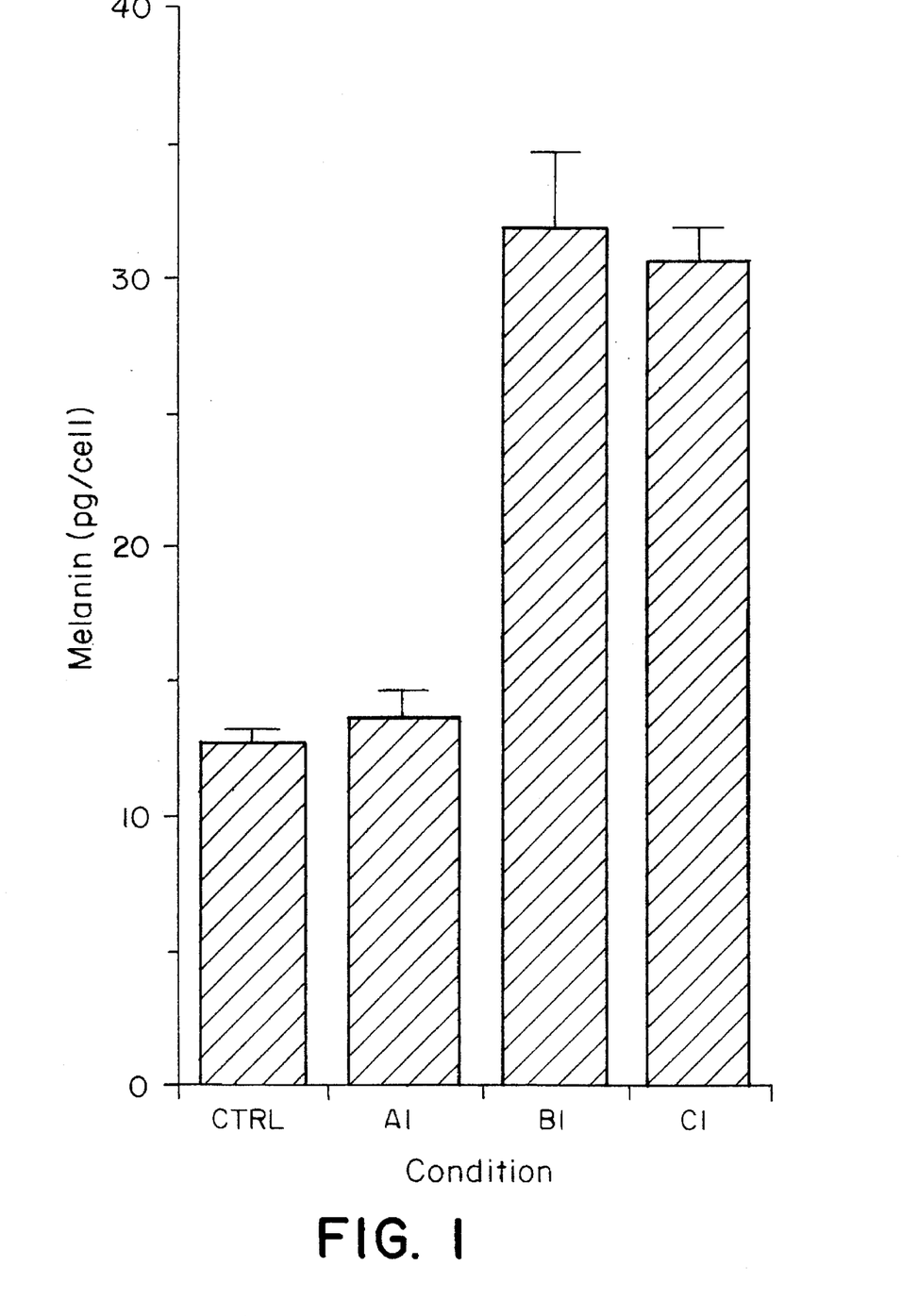
FIG. 1 is a graph depicting the effect on pigmentation of the exposure of S91 cells to DNA fragments in a phospholipid carrier. CTRL=control (no liposomes or DNA fragments); A1=empty liposomes (no DNA fragments); B1=liposomes containing UV-DNA (irradiated); C1=liposomes containing DNA (not irradiated).

The results of this experiment, as shown in FIG. 1, indicate that the addition of liposomes containing UV-DNA stimulated melanin production to a greater extent than the addition of empty liposomes or liposomes containing non-irradiated DNA; the addition of liposomes containing non-irradiated DNA stimulated melanin production in comparison to empty liposomes and the control.

In a second experiment, S91 cells were plated at $3 \times 10^5$ cells per dish on 60 mm culture dishes, in DME plus 10% CS at 37° C., and cultured for 24 hours (Day 1). On Day 2, the medium was changed, and cells were exposed to one of five additions: 100 µM empty liposomes ($A_1$); 100 µM liposomes containing UV-DNA (irradiated) ($B_1$); 100 µM liposomes containing DNA (not irradiated) ($C_1$); 100 µl (10 mg/ml) DNA (non-encapsulated (i.e. not within liposomes), and not irradiated); or 100 µl (10 mg/ml) DNA plus 10 minutes of UVC (non-encapsulated, and irradiated). The cells were then cultured for two days; on Day 4, the medium was changed and the cells were cultured for another three days in the presence of the respective additions. On Day 7 the cells were collected, and assayed for melanin.

Figure 2:
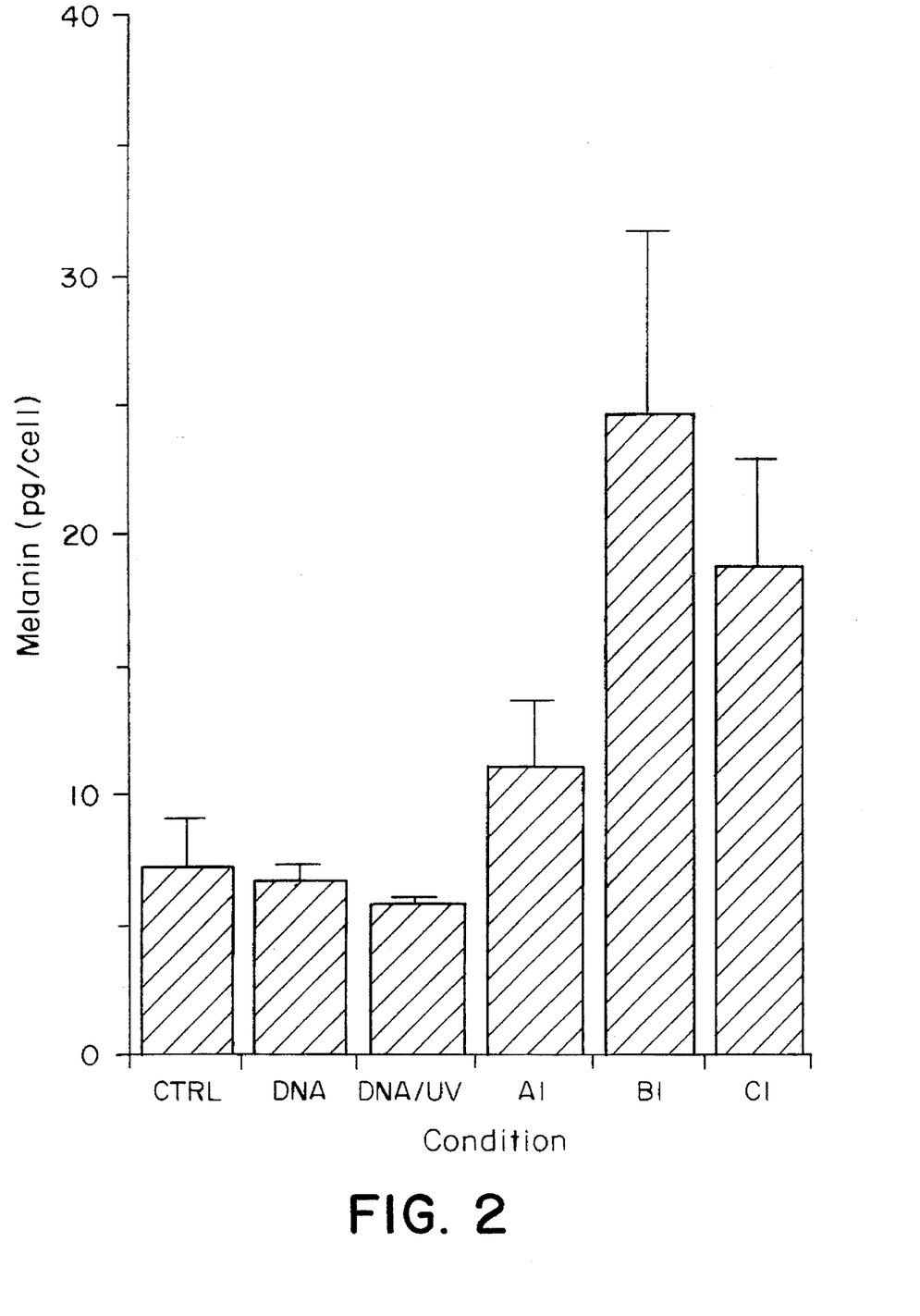
FIG. 2 is a graph depicting the effect on pigmentation of the exposure of S91 cells to DNA fragments. CTRL=control (no liposomes or DNA fragments); DNA=100 µl (10 mg/ml) DNA; DNA/UV=100 µl (10 mg/ml) DNA irradiated for 10 minutes with UVC; A1=empty liposomes (no DNA fragments); B1=liposomes containing UV-DNA (irradiated); C1=liposomes containing DNA (not irradiated).

The results of this experiment, as shown in FIG. 2, indicate that the addition of liposomes containing UV-DNA stimulated melanin production to a greater extent than the addition of empty liposomes, liposomes containing non-irradiated DNA, non-encapsulated DNA, or non-encapsulated UV-irradiated DNA. The addition of liposomes containing non-irradiated DNA stimulated melanin production to a greater extent than did the addition of empty liposomes, non-encapsulated DNA, or non-encapsulated UV-irradiated DNA.

Figure 3:
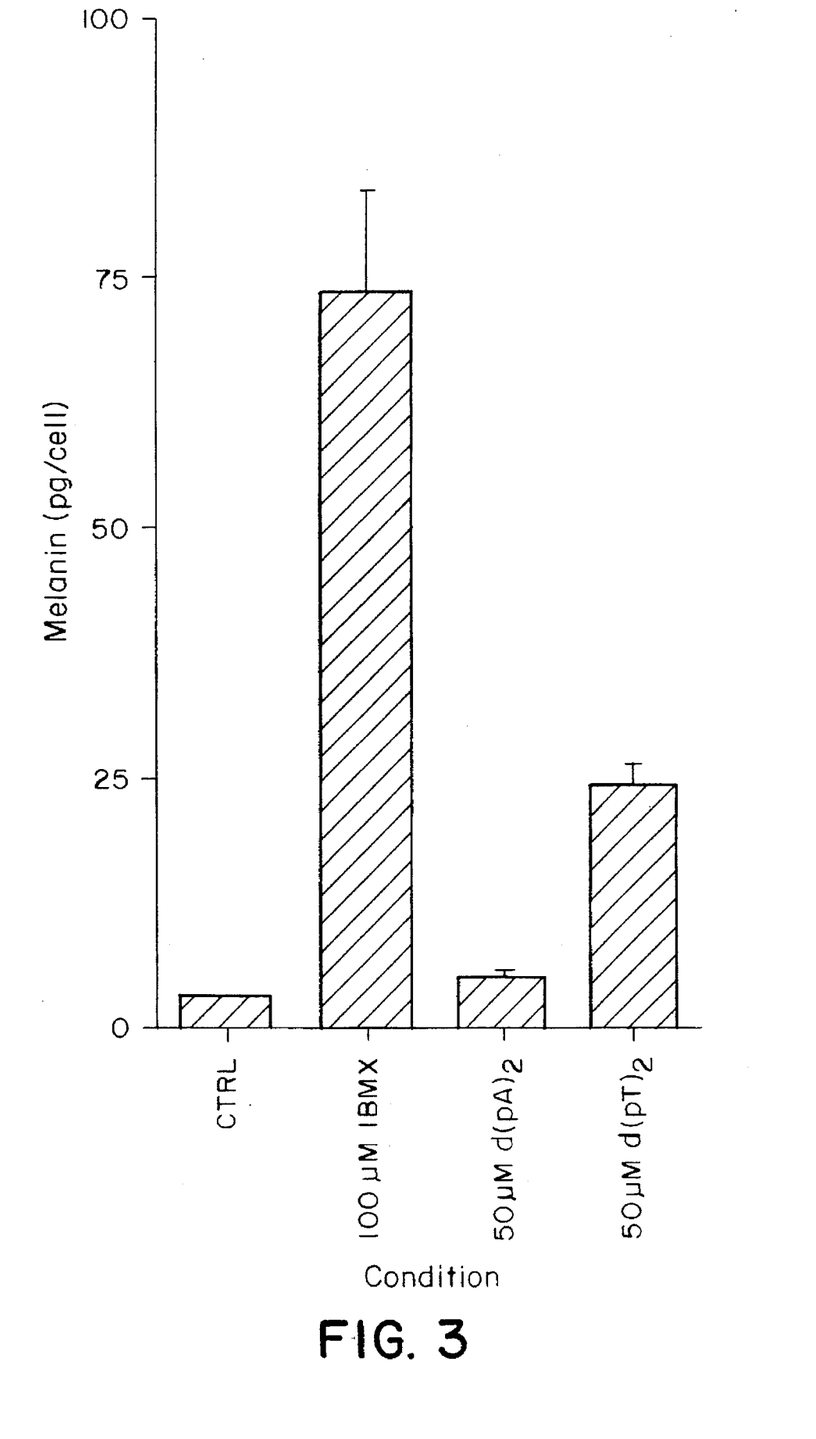
FIG. 3 is a graph depicting the effect on pigmentation of the exposure of S91 cells to the dinucleotides $d(pT)_2$ and $d(pA)_2$ when cultured. CTRL=Control (no additions); IBMX=isobutylmethylxanthine (a positive control); $d(pA)_2$=deoxyadenylic acid dinucleotide; and $d(pT)_2$=thymidylic acid dinucleotide.

In a third experiment, S91 cells were plated on 60 mm culture dishes in DME plus 10% calf serum (CS) at a density of $2 \times 10^5$ cells/dish. Two days later, the medium was changed and fresh DME plus 10% CS was added, along with either 50 µM deoxyadenylic acid dinucleotide ($d(pA)_2$), 50 µM thymidylic acid dinucleotide ($d(pT)_2$) or 100 µM isobutylmethylxanthine (IBMX), a known stimulator of melanogenesis in S91 cells, as a positive control. Four days later, the cells were collected and counted and an equal number of cells was pelleted for calculation of melanin/cell based on $OD_{475}$. FIG. 3 shows that while 50 µM $d(pA)_2$ yielded a 50% increase in melanin/cell compared to nontreated controls, $d(pT)_2$ gave a 7-fold increase. As is normally observed, IBMX stimulated pigmentation approximately 15-fold above background.

Figure 4:
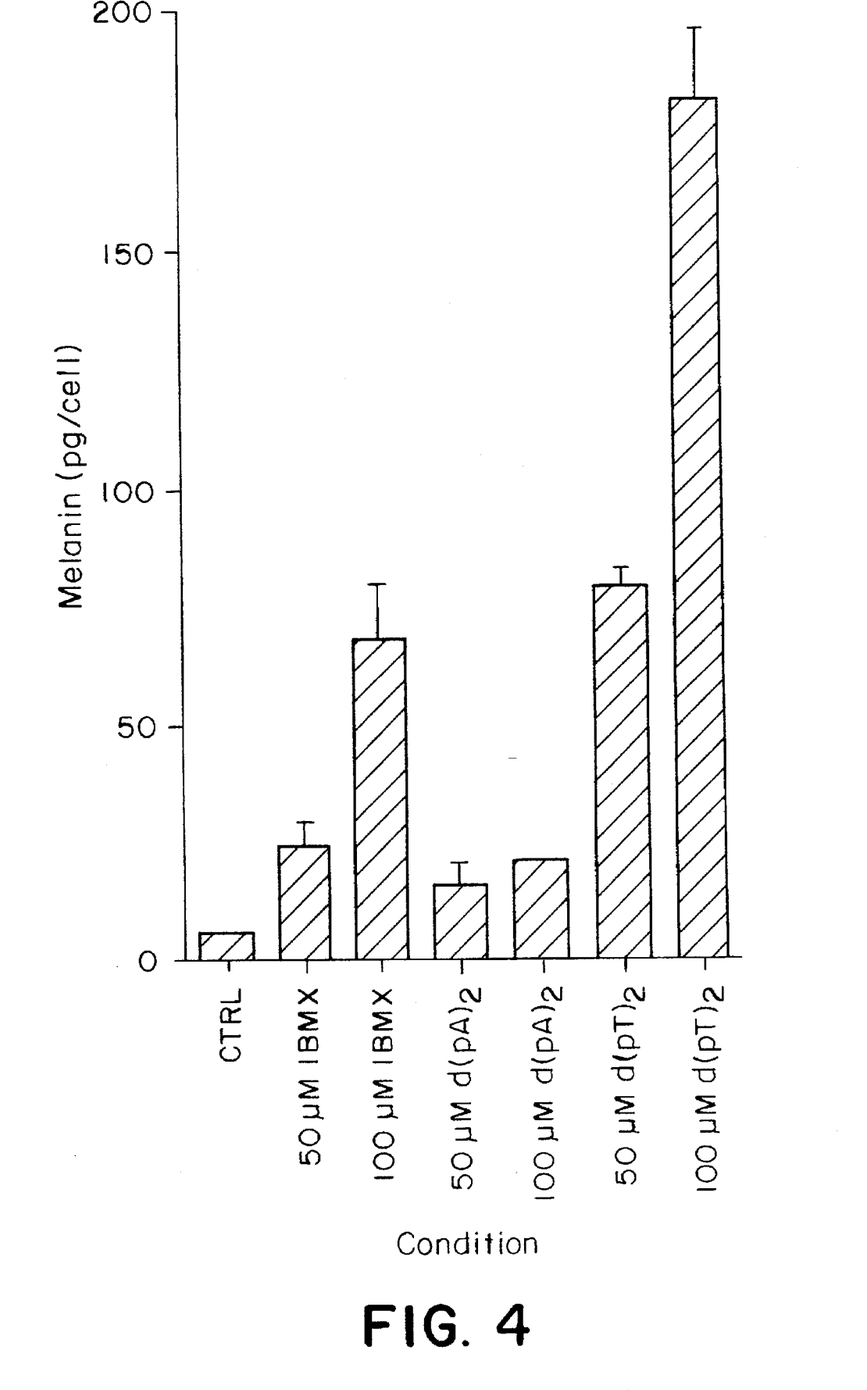
FIG. 4 is a graph depicting the effect on pigmentation of exposure of S91 cells to deoxydinucleotides $d(pA)_2$ and $d(pT)_2$ when cultured in a medium of DME plus 2% calf serum (CS). CTRL=Control (no additions); IBMX=isobutylmethylxanthine (a positive control); $d(pA)_2$=deoxyadenylic acid dinucleotide; and $d(pT)_2$=thymidylic acid dinucleotide.

In a fourth experiment, S91 cells were plated at a density of $20 \times 10^5$ cells/dish and grown for 3 days in DME plus 10% CS. On the fourth day, the medium was changed to DME plus 2% CS to slow cell proliferation. At this time, plates were either non-supplemented (controls) or given 50 µM or 100 µM IBMX, $d(pA)_2$ or $d(pT)_2$. After 3 days, the cells were collected and the melanin/cell calculated. The results are represented in FIG. 4. The cells exposed to $d(pT)_2$ showed a dose-dependent increase in melanin/cell with 50 µM $d(pT)_2$ and 100 mm $d(pT)_2$ showing a 13 and 30-fold increase respectively compared to control exposed to $d(pA)_2$ showed a three to four-fold increase in melanin content. 100 µM IBMX gave a nearly 15-fold increase in pigmentation above the negative control, as expected.

Figure 5:
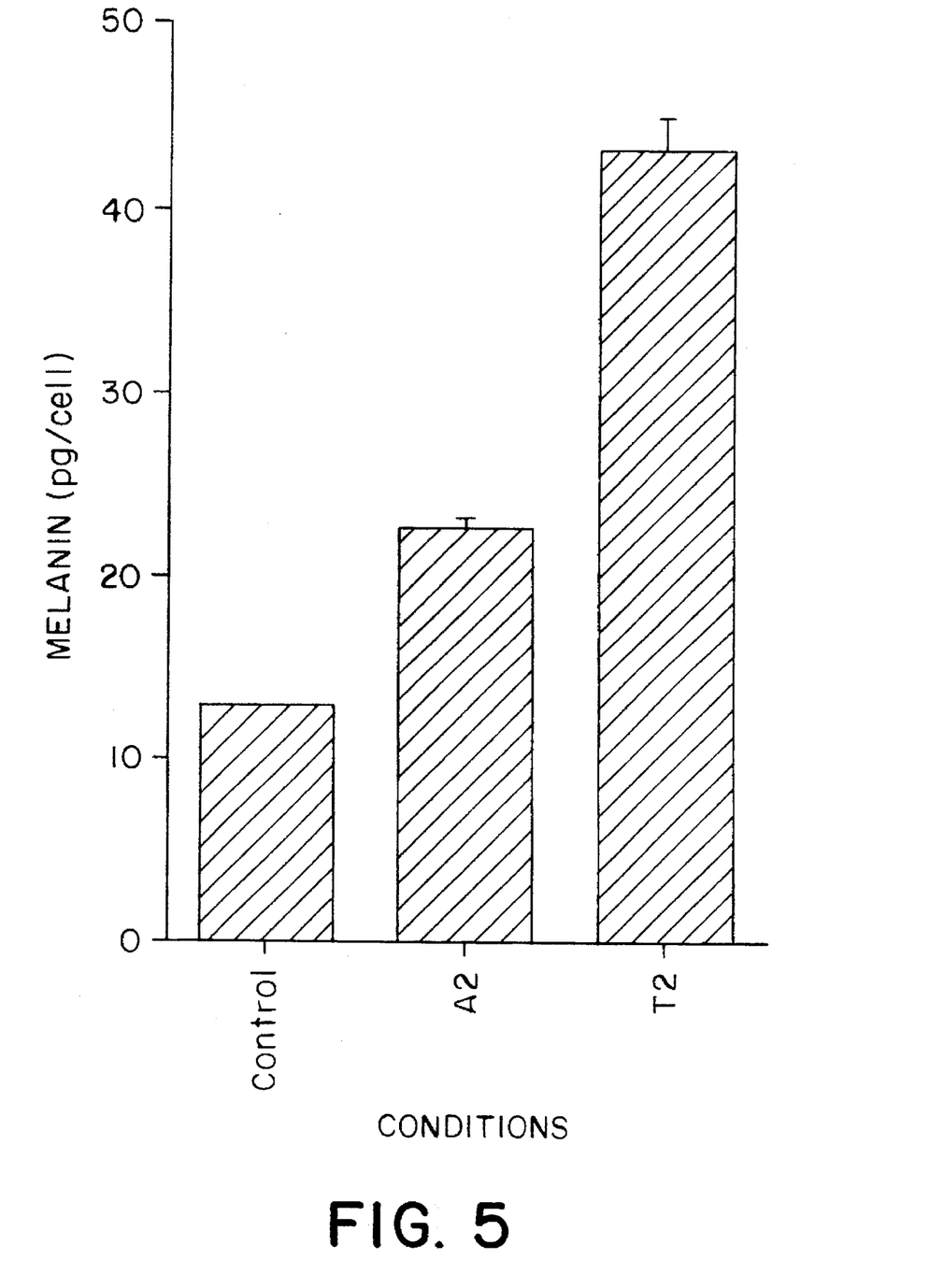
FIG. 5 is a graph depicting the effect on pigmentation of exposure of S91 cells to deoxynucleotides $d(pA)_2$ and $d(pT)_2$ and/or to IBMX when cultured in a medium of DME plus 2% calf serum (CS). CTRL=Control (water only); IBMX=isobutylmethylxanthine; A2=$d(pA)_2$ (deoxyadenylic acid dinucleotide); T2=$d(pT)_2$ (thymidylic acid dinucleotide); A2/IBMX=$d(pA)_2$ and IBMX; T2/IBMX=$d(pT)_2$ and IBMX.

In a fifth experiment, S91 cells were plated on 60 mm culture dishes in DME plus 2% calf serum (CS) at a density of $2 \times 10^5$ cells/dish. Plates were dosed with either 150 µl water (control), 100 µM $d(pA)_2$, or 100 µM $d(pT)_2$. Four days later, the cells were collected and the melanin/cell was calculated. FIG. 5 shows that both $d(pA)_2$ and $d(pT)_2$ gave an increase in melanin over the control.

Figure 6:
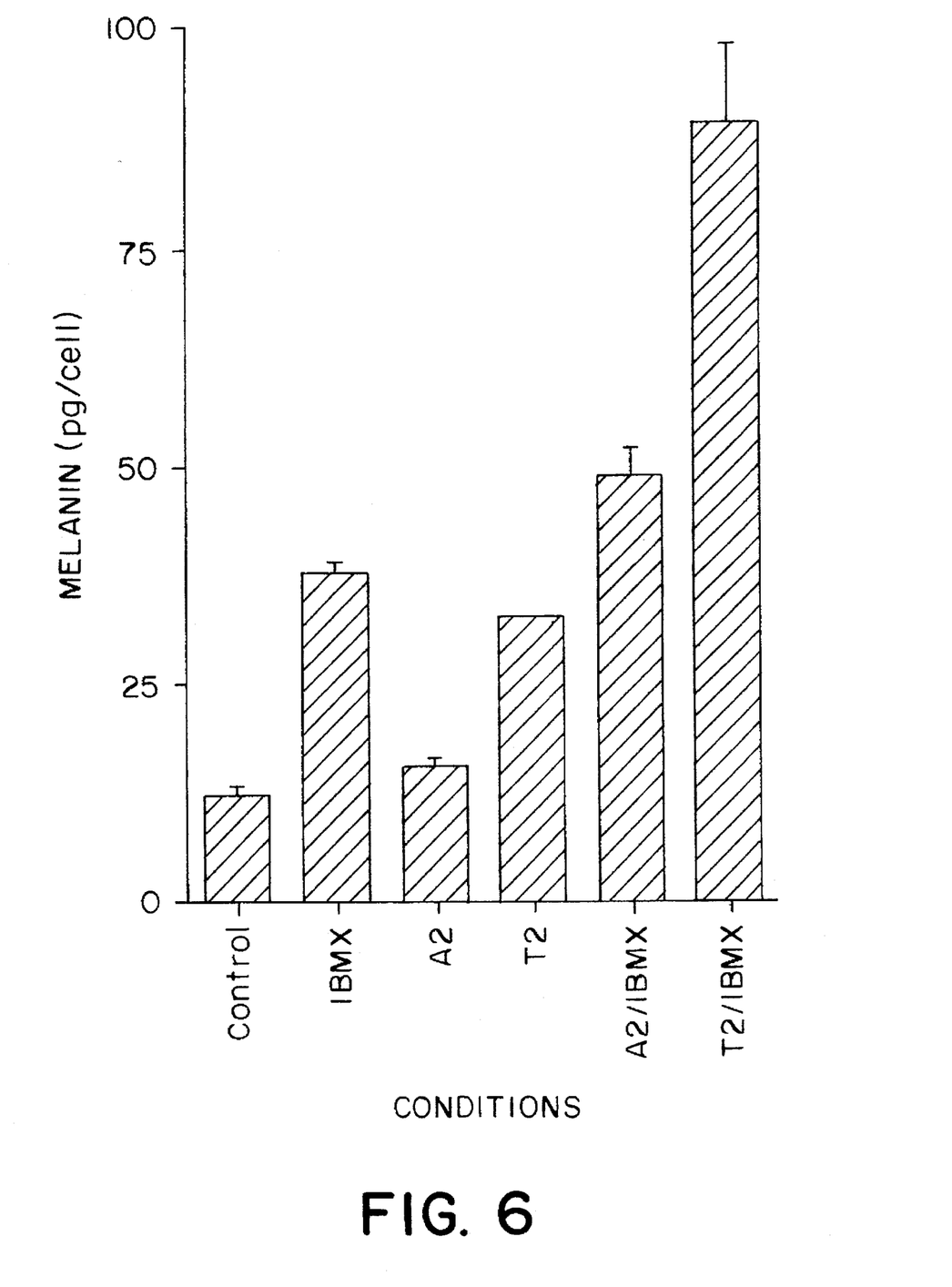
FIG. 6 a graph depicting the effect on pigmentation of exposure of S91 cells to deoxynucleotides $d(pA)_2$ and $d(pT)_2$ when cultured in a medium of DME plus 2% calf serum (CS). Control (water only); A2=d(pA)2 (deoxyadenylic acid dinucleotide); T2=d(pT)$_2$ (thymidylic acid dinucleotide).

In a sixth experiment, S91 cells were plated at a density of $1 \times 10^5$ cells/dish and grown in DME plus 2% CS. On Day 1, a first (control) plate and a second plate were each given 150 µl water; a third and fourth plate were each given 150 µl $d(pT)_2$ stock solution (final concentration of dinucleotides was 100 µM); and a fifth and sixth plate were each given 150 µl $d(pA)_2$ stock solution (final concentration of dinucleotides was 100 µM). On Day 3, the second, fourth and sixth plates were dosed with 100 µM IBMX, and the first (control), third and fifth plates were non-supplemented. On Day 6, the cells were collected and the melanin/cell calculated. The results are represented in FIG. 6. The cells exposed to IBMX alone, $d(pT)_2$, or $d(pA)_2$ showed an increase in melanin/cell compared to controls. Cells exposed to $d(pA)_2$/IBMX or $d(pT)_2$/IBMX showed an increase in melanin content over the cells exposed to IBMX, $d(pT)_2$, or $d(pA)_2$ alone. Cells exposed to $d(pA)_2$/IBMX, and particularly to $d(pT)_2$/IBMX demonstrated a synergistic (greater than additive) increase in melanin.

Figure 7:
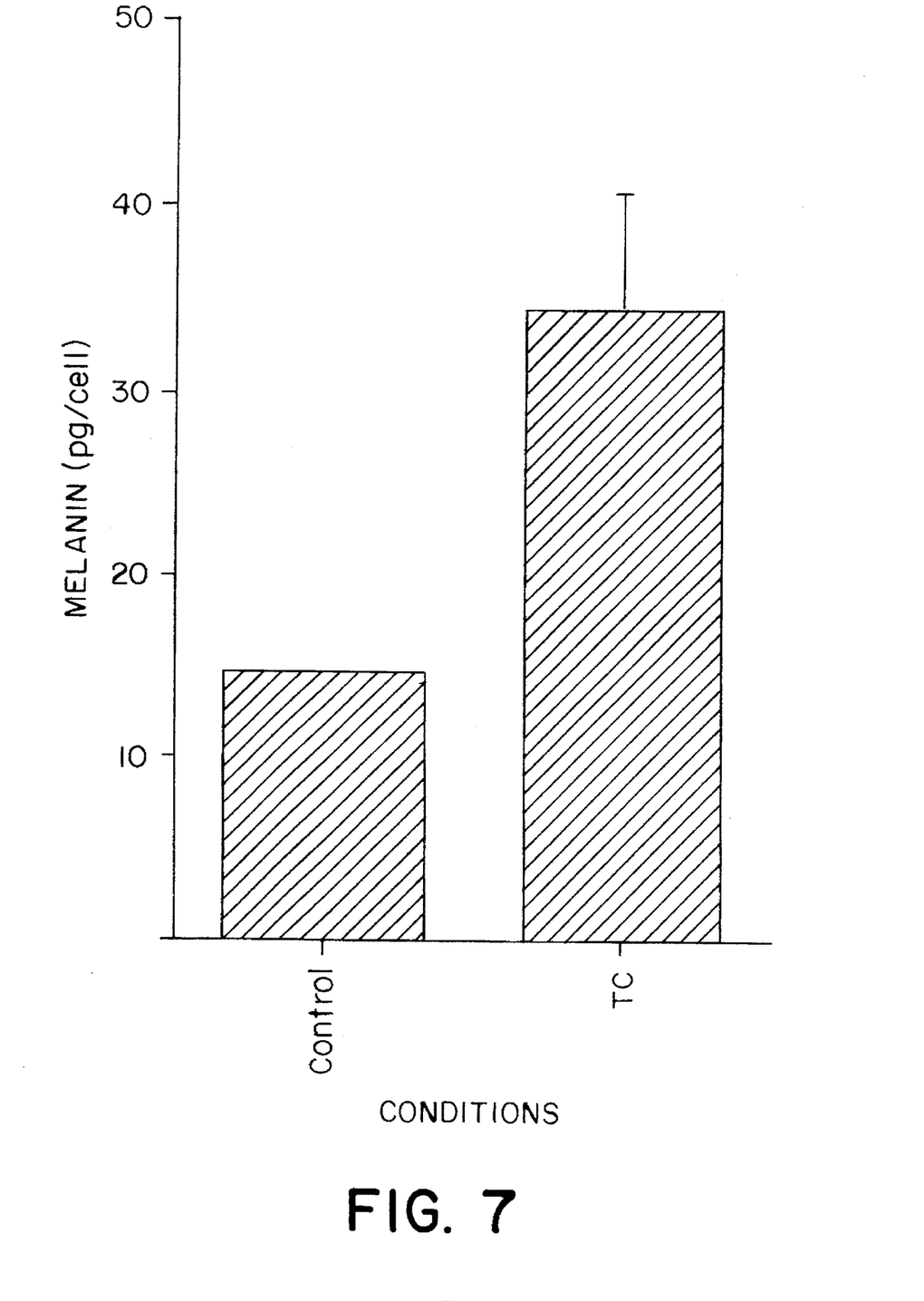
FIG. 7 is a graph depicting the effect on pigmentation of exposure of S91 cells to deoxynucleotide pTdpC when cultured in a medium of DME plus 2% calf serum (CS). Control (water only); TC=d(pTpC).

In a seventh experiment, S91 cells were plated on 60 mm culture dishes in DME plus 2% calf serum (CS) at a density of $1 \times 10^5$ cells/dish. Plates were dosed with either 150 µl water (control) or 100 µM d(pTpC). Six days later, the cells were collected and the melanin/cell was calculated. FIG. 7 shows that dTpdC gave a significant increase in melanin over the control.

In further testing carried out using a similar protocol, the S91 cells were dosed with TpT. Preliminary results indicated that TpT showed no significant increase of the melanin/cell over the control level.

EXAMPLE 2

Effect of DNA Fragments on the Pigmentation of Melanocytes

Figure 8:
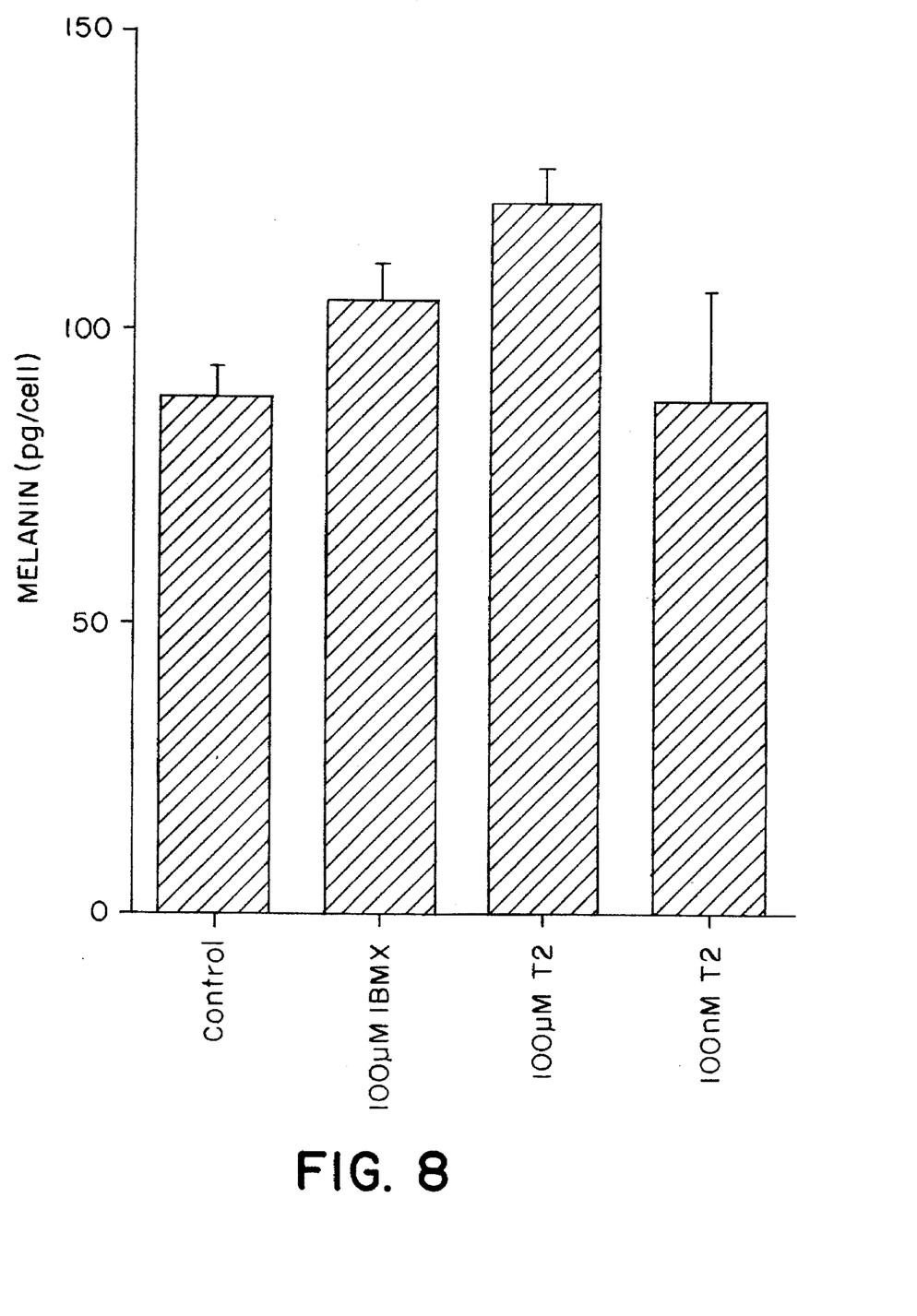
FIG. 8 is a graph depicting the effect on pigmentation of exposure of melanocytes cells to deoxynucleotides d(pT)$_2$ or to IBMX when cultured in a medium of DME plus 10% calf serum (CS). CTRL=Control; IBMX= isobutylmethylxanthine; T2=d(pT)$_2$ (thymidylic acid dinucleotide).

Human melanocytes obtained from a black donor were cultured in DME plus 10% CS, 20 ng/ml epidermal growth factor (EGF), 10 ng/ml fibroblast growth factor (FGF), and 1.2 nM cholera toxin. On day 1, plates were exposed to one of four treatments: nothing (control), 100 µM IBMX, 100 µM d(pT)$_2$, or 100 nm d(pT)$_2$. On days 2 and 3, plates were given fresh medium and another dose of the same treatment as on day 1. On day 7, the cells were collected and the melanin/cell calculated. The results are represented in FIG. 8. The cells exposed to IBMX alone, or d(pT)$_2$ showed an increase in melanin/cell compared to the control.

EXAMPLE 3

Effect of DNA Fragments on the Pigmentation of Guinea Pig Epidermis

Two guinea pigs (designated Animal G and Animal H) were exposed to a series of solutions to determine the effect of thymidine dinucleotides on skin pigmentation. The number assigned to each solution, and the composition of the solution, are shown below in the Table.

Solutions were applied twice daily for five consecutive days. Each solution was applied to a separate region, identified as an "application site", of the dorsal epidermis of each animal. Animals were denuded prior to the first application and upon subsequent observations. The animals were maintained during the experiment in a confined room under normal, natural daylight or normal, artificial daylight, excluding any specific exposure to ultraviolet irradiation. Animals were photographed prior to the first application (day 1), during the experiment (days 7, 14, 21), and prior to surgical biopsies (day 26). The animals were observed for changes, and especially increases, in skin pigmentation; a scale ranging from 0 (no change in pigmentation) to +3 (greatest increase in pigmentation), having increments of 0, +/−, +1, +2, and 3, was used to grade the changes of skin pigmentation. The results of the experiment are shown below in the Table.

TABLE

Solutions Utilized in Guinea Pig Study

| Sol. No. | Composition of Solution | Animal | Changes in Skin Pigmentation | | | |
|---|---|---|---|---|---|---|
| | | | Day 7 | Day 14 | Day 21 | Day 26 |
| 1 | PG vehicle control | G | 0 | 0 | 0 | 0 |
| | | H | 0 | 0 | +/− | +1 |
| 2 | 3:1 PG:DMSO vehicle control | G | 0 | 0 | +/− | +/− |
| | | H | * | 0 | +/− | +1 |
| 3 | 100 µM d(pT)$_2$ in PG | G | 0 | 0 | +/− | +/− |
| | | H | * | 0 | +2 | |
| 4 | 100 µM d(pT)$_2$ in 3:1 PG:DMSO | G | 0 | 0 | +/− | +/− |
| | | H | * | 0 | +/− | +2 |
| 5 | 300 µM d(pT)$_2$ in PG | G | 0 | 0 | +/− | +1 |
| | | H | * | 0 | +/− | +1 |
| 6 | 300 µM d(pT)$_2$ in 3:1 PG:DMSO | G | 0 | 0 | +/− | +1 |
| | | H | * | 0 | +1 | +2 |

Sol. No. = solution number; PG = propylene glycol; DMSO = dimethyl sulfoxide.
*slight irritation.

As shown in the Table, both animals demonstrated a slight increase in pigmentation on day 21, and a more pronounced increase in pigmentation on day 26. Biopsies from an untreated site, as well as from the sites for solutions 1 and 3 of Animal H, indicated greater concentration of melanin in the site treated with solution 3(100 µM p(dT)$_2$ in propylene glycol) than in either the untreated site or the site treated with the control PG solutions (data not shown).

EXAMPLE 4

Emulsion of the Current Invention

Three different phases were combined to form the preparation.

| Phase A: | |
|---|---|
| Salmon sperm DNA fragments | 0.2 g |
| Deoxynucleotide d(TpT) | 0.02 g |
| Distilled water | 10 g |
| Phase B: | |
| 1-oleoyl-2-acetyl-glycerol | 0.5 g |
| Miglyol 812 | 10 g |
| Phase C: | |
| Excipient for emulsion (including Miglyol 812 10% and Carbopol 1342 2%) sufficient for 100 g | |

The water solution of salmon sperm DNA fragments was prepared by a standard autoclaving process. Phase A was prepared by mixing the components at room temperature. A moderate heating at 30° C. was preferred for preparing Phase B. Phase A and Phase B were emulsified into Phase C by standard emulsifying processes. Autoclaving and emulsifying processes are well known to those skilled in the art. The resulting emulsion, when applied on the skin, will stimulate tanning even without specific sunlight exposure.

EXAMPLE 5

Liposomal Gel of the Current Invention

Two different phases were combined to form the preparation.

| Phase A: | |
|---|---|
| Soya phospholipids | 0.9 g |
| Beta-sitosterol | 0.1 g |
| Deoxynucleotide d(pT)$_2$ | 0.001 g |
| Water sufficient for | 50 g |
| Phase B: | |
| Carbopol 941 gel at 2% in water Gel sufficient for | 50 g |

In a first step, a spray-dried powder is prepared from a solution of phospholipids and beta-sitosterol (phase A) according to the process described in U.S. Pat. No. 4,508,703. This powder is then dispersed into an aqueous solution of the other ingredients in Phase A, stirred during one hour, and homogenized under pressure, according to the process described in the U.S. Pat. No. 4,621,023 to obtain a liposomal suspension.

The liposomal suspension is then mixed with the same weight of Carbopol gel (Phase B).

The resulting liposomal gel can be applied, preferably once a day in the morning, on the skin to obtain a cosmetic tanning response or protection against the nocive effect of sun, irrespective of sun exposure.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method for protecting the epidermis of a mammal against ultraviolet damage comprising applying topically to the epidermis DNA fragments selected from the group consisting of: single-stranded DNA fragments, double-stranded DNA fragments, a mixture of single-and double-stranded DNA fragments, deoxynucleotides, dinucleotides, and dinucleotide dimers, in a sufficient quantity to stimulate melanin production.

2. The method of claim 1 wherein the DNA fragments are approximately 2–200 bases in length.

3. The method of claim 1 wherein the dinucleotides are selected from the group consisting of: $d(pT)_2$, $d(pC)_2$, $d(pA)_2$, $d(pCpT)$, $d(pTpC)$, $d(CpT)$ and $d(TpC)$.

4. The method of claim 1 wherein said single-stranded DNA fragments, double-stranded DNA fragments, mixture of single- and double-stranded DNA fragments, deoxynucleotides, or dinucleotides are ultraviolet-irradiated.

5. The method of claim 1 wherein the dinucleotide dimers are dimers of dinucleotides selected from the group consisting of: $d(pT)_2$, $d(pC)_2$, $d(pA)_2$, $d(pCpT)$, $d(pTpC)$, $d(CpT)$ and $d(TpC)$.

6. The method of claim 1 wherein the DNA fragments are administered in a liposomal preparation.

7. The method of claim 1 wherein the DNA fragments are administered in propylene glycol.

8. The method of claim 1 wherein the concentration of said DNA fragments ranges between 0.1 µM and 1 mM.

9. The method of claim 1 one of wherein the mammal is a human.

10. The method of claim 1 wherein the DNA fragments are present in combination with a diacyl glycerol.

11. The method of claim 1 wherein the DNA fragments are present in combination with isobutylmethylxanthine.

12. A method for stimulating pigmentation of the skin of a mammal, comprising applying topically to the epidermis of the mammal DNA fragments selected from the group consisting of: single-stranded DNA fragments, double-stranded DNA fragments, a mixture of single- and double-stranded DNA fragments, deoxynucleotides, dinucleotides, and dinucleotide dimers, in a sufficient quantity to stimulate melanin production.

13. The method of claim 12 wherein the DNA fragments are approximately 2–200 bases in length.

14. The method of claim 12 wherein the dinucleotides are selected from the group consisting of: $d(pT)_2$, $d(pC)_2$, $d(pA)_2$, $d(pCpT)$, $d(pTpC)$, $d(CpT)$ and $d(TpC)$.

15. The method of claim 12 wherein the dinucleotide dimers are dimers of dinucleotides selected from the group consisting of: $d(pT)_2$, $d(pC)_2$, $d(pA)_2$, $d(pCpT)$, $d(pTpC)$, $d(CpT)$ and $d(TpC)$.

16. The method of claim 12 wherein said single-stranded DNA fragments, double-stranded DNA fragments, mixture of single- and double-stranded DNA fragments, deoxynucleotides, or dinucleotides are ultraviolet-irradiated.

17. The method of claim 12 wherein the DNA fragments are administered in a liposomal preparation.

18. The method of claim 12 wherein the DNA fragments are administered in propylene glycol.

19. The method of claim 12 wherein the DNA fragments are present in combination with a diacyl glycerol.

20. The method of claim 12 wherein the DNA fragments are present in combination with isobutylmethylxanthine.

21. The method of claim 12 wherein the mammal is a human.

22. The method of claim 12 wherein the concentration of the DNA fragments ranges between 0.1 µM and 1 mM.

\* \* \* \* \*